US012788499B2

(12) United States Patent
Tang et al.

(10) Patent No.: US 12,788,499 B2
(45) Date of Patent: Nov. 10, 2026

(54) APPARATUS AND METHOD TO DETERMINE ENDOSCOPE ROLL ORIENTATION BASED ON IMAGE ANALYSIS

(71) Applicants: Acclarent, Inc., Irvine, CA (US); Biosense Webster (Israel) Ltd., Yokneam (IL)

(72) Inventors: Raymond Yue-sing Tang, Rosemead, CA (US); Shubhayu Basu, Anaheim, CA (US); Alex Gonzalez, Lake Forest, CA (US); Gigi Koe, Anaheim, CA (US)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 157 days.

(21) Appl. No.: 18/533,736

(22) Filed: Dec. 8, 2023

(65) Prior Publication Data

US 2024/0238048 A1 Jul. 18, 2024

Related U.S. Application Data

(60) Provisional application No. 63/438,603, filed on Jan. 12, 2023.

(51) Int. Cl.

*A61B 34/20* (2016.01)
*A61B 1/018* (2006.01)

(Continued)

(52) U.S. Cl.

CPC .............. *A61B 34/20* (2016.02); *A61B 1/018* (2013.01); *A61B 1/05* (2013.01); *A61B 5/065* (2013.01); *A61B 2034/2051* (2016.02)

(58) Field of Classification Search

CPC ........... A61B 34/20; A61B 1/018; A61B 1/05; A61B 5/065; A61B 2034/2051;

(Continued)

(56) References Cited

U.S. PATENT DOCUMENTS 7,720,521 B2 5/2010 Chang et al.
8,644,913 B2 * 2/2014 Simpson .............. A61B 5/0062 600/478

(Continued)

FOREIGN PATENT DOCUMENTS

CN 108113629 A 6/2018
CN 108938086 A 12/2018

*Primary Examiner* — Baisakhi Roy
(74) *Attorney, Agent, or Firm* — Barnes & Thornburg LLP

(57) ABSTRACT

An apparatus includes a shaft assembly. The shaft assembly includes a working channel, a distal end, an image sensor, a navigation sensor, and a reference marker. The working channel is sized to receive a working element. The distal end includes an opening that is positioned to allow a working element in the working channel to pass through the distal end. The image sensor has a field of view distal to the distal end such that the image sensor is configured to capture at least one image providing a field of view distal to the distal end. The navigation sensor is configured to generate signals indicative of a position of the distal end in three-dimensional space. The reference marker is positioned within the field of view of the image sensor, the reference marker being fixed against movement relative to the image sensor.

20 Claims, 7 Drawing Sheets

(51) Int. Cl.

*A61B 1/05* (2006.01)

*A61B 5/06* (2006.01)

(58) Field of Classification Search

CPC ............ A61B 1/00097; A61B 1/00057; A61B 1/00193; A61B 2034/2065

See application file for complete search history.

(56) References Cited

U.S. PATENT DOCUMENTS

| | | | | |
|---|---|---|---|---|
| 9,345,406 | B2 * | 5/2016 | Spencer ......... | A61B 17/320758 |
| 9,427,172 | B2 | 8/2016 | Eichler et al. | |
| 9,438,897 | B2 | 9/2016 | Barreto et al. | |
| 10,463,242 | B2 | 11/2019 | Kesten et al. | |
| 10,561,370 | B2 | 2/2020 | Salazar et al. | |
| 10,955,657 | B2 | 3/2021 | Shameli et al. | |
| 11,376,401 | B2 | 7/2022 | Matlock et al. | |
| 11,457,981 | B2 | 10/2022 | Govari et al. | |
| 2006/0161211 | A1 * | 7/2006 | Thompson ............. | A61N 1/368 607/19 |
| 2014/0364725 | A1 | 12/2014 | Makower | |
| 2015/0223725 | A1 * | 8/2015 | Engel ..................... | A61B 34/20 600/417 |
| 2016/0000515 | A1 * | 1/2016 | Sela ....................... | A61B 34/10 600/424 |
| 2016/0338803 | A1 * | 11/2016 | Pesach ...................... | G06T 7/74 |
| 2017/0157361 | A1 * | 6/2017 | Barrish ............ | A61B 17/00234 |
| 2020/0107885 | A1 | 4/2020 | Palushi et al. | |
| 2020/0107886 | A1 * | 4/2020 | Govari ............... | A61B 1/00194 |
| 2020/0196851 | A1 | 6/2020 | Shameli et al. | |
| 2021/0361912 | A1 | 11/2021 | Matlock et al. | |
| 2021/0369355 | A1 * | 12/2021 | Masaki ................ | A61B 5/6852 |
| 2022/0110513 | A1 | 4/2022 | Palushi et al. | |
| 2022/0257093 | A1 | 8/2022 | Tarke et al. | |

* cited by examiner

APPARATUS AND METHOD TO DETERMINE ENDOSCOPE ROLL ORIENTATION BASED ON IMAGE ANALYSIS

PRIORITY

This application claims the benefit of U.S. Pat. App. No. 63/438,603, entitled "Apparatus and Method to Determine Endoscope Roll Orientation Based on Image Analysis," filed Jan. 12, 2023, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation system that may be used in IGS procedures is the CARTO® 3 System by Biosense-Webster, Inc., of Irvine, California. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus.

It may also be desirable to ablate tissue within the ear, nose, or throat of a patient. For instance, such ablation may be desirable to remodel tissue (e.g., to reduce the size of a turbinate), to provide denervation (e.g., to disable the posterior nasal nerve), and/or for other purposes. To achieve ablation, an end effector with one or more needle electrodes or other kind(s) of tissue contacting electrodes may be activated with monopolar or bipolar RF energy. Such ablation procedures may be carried out in conjunction with a dilation procedure or separately from a dilation procedure.

It may also be desirable to provide easily controlled placement of a dilation catheter, ablation instrument, or other ENT instrument in an anatomical passageway, including in procedures that will be performed only by a single operator. While several systems and methods have been made and used to position an ENT instrument in an anatomical passageway, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Example of an Image Guided Surgery Navigation System

Figure 1:
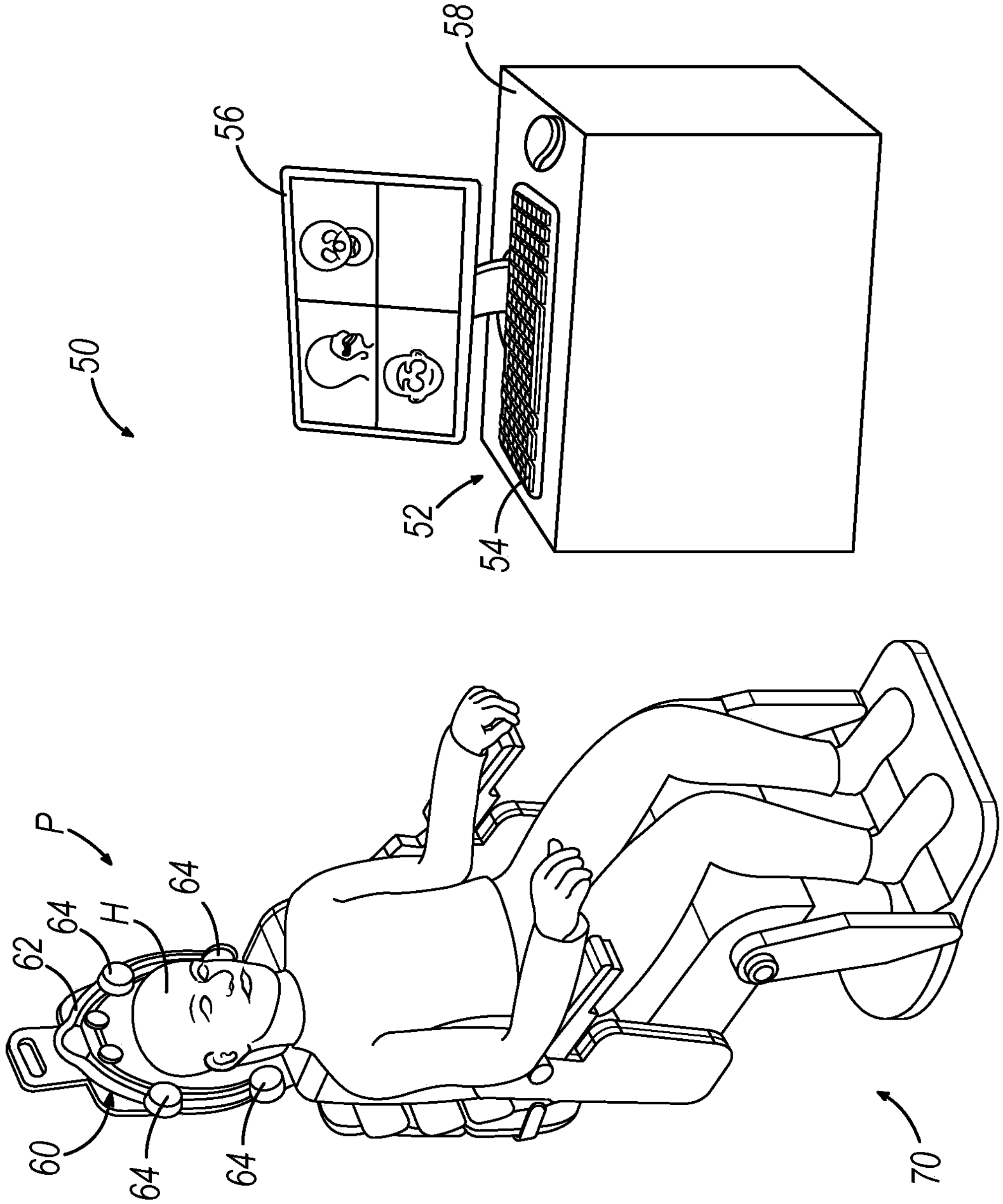
FIG. 1 depicts a schematic view of an example of a surgery navigation system being used on a patient seated in an example of a medical procedure chair.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an example of a IGS navigation system (50) enabling an ENT procedure to be performed using image guidance. In addition to or in lieu of having the components and operability described herein IGS navigation system (50) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (50) of the present example comprises a field generator assembly (60), which comprises set of magnetic field generators (64) that are integrated into a horseshoe-shaped frame (62). Field generators (64) are operable to generate alternating magnetic fields of different frequencies around the head (H) of the patient (P). An instrument, such as any of the RF ablation instruments described below, may be inserted into the head (H) of the patient (P). Such an instrument may be a standalone device or may be positioned on an end effector. In the present example, frame (62) is mounted to a chair (70), with the patient (P) being seated in the chair (70) such that frame (62) is located adjacent to the head (H) of the patient (P). By way of example only, chair (70) and/or field generator assembly (60) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein.

IGS navigation system (50) of the present example further comprises a processor (52), which controls field generators (64) and other elements of IGS navigation system (50). For instance, processor (52) is operable to drive field generators (64) to generate alternating electromagnetic fields; and process signals from the instrument to determine the location of a navigation sensor in the instrument within the head (H) of the patient (P). Processor (52) comprises a processing unit (e.g., a set of electronic circuits arranged to evaluate and execute software instructions using combinational logic circuitry or other similar circuitry) communicating with one or more memories. Processor (52) of the present example is mounted in a console (58), which comprises operating controls (54) that include a keypad and/or a pointing device such as a mouse or trackball. A physician uses operating controls (54) to interact with processor (52) while performing the surgical procedure.

While not shown, the instrument may include a navigation sensor that is responsive to positioning within the alternating magnetic fields generated by field generators (64). A coupling unit (not shown) may be secured to the proximal end of the instrument and may be configured to provide communication of data and other signals between console (58) and the instrument. The coupling unit may provide wired or wireless communication of data and other signals.

In some versions, the navigation sensor of the instrument may comprise at least one coil at or near the distal end of the instrument. When such a coil is positioned within an alternating electromagnetic field generated by field generators (64), the alternating magnetic field may generate electrical current in the coil, and this electrical current may be communicated along the electrical conduit(s) in the instrument and further to processor (52) via the coupling unit. This phenomenon may enable IGS navigation system (50) to determine the location of the distal end of the instrument within a three-dimensional space (i.e., within the head (H) of the patient (P), etc.). To accomplish this, processor (52) executes an algorithm to calculate location coordinates of the distal end of the instrument from the position related signals of the coil(s) in the instrument.

Processor (52) uses software stored in a memory of processor (52) to calibrate and operate IGS navigation system (50). Such operation includes driving field generators (64), processing data from the instrument, processing data from operating controls (54), and driving display screen (56). In some implementations, operation may also include monitoring and enforcement of one or more safety features or functions of IGS navigation system (50). Processor (52) is further operable to provide video in real time via display screen (56), showing the position of the distal end of the instrument in relation to a video camera image of the patient's head (H), a CT scan image of the patient's head (H), and/or a computer-generated three-dimensional model of the anatomy within and adjacent to the patient's nasal cavity. Display screen (56) may display such images simultaneously and/or superimposed on each other during the surgical procedure. Such displayed images may also include graphical representations of instruments that are inserted in the patient's head (H), such that the operator may view the virtual rendering of the instrument at its actual location in real time. By way of example only, display screen (56) may provide images in accordance with at least some of the teachings of U.S. Pat. No. 10,463,242, entitled "Guidewire Navigation for Sinuplasty," issued Nov. 5, 2019, the disclosure of which is incorporated by reference herein. In the event that the operator is also using an endoscope, the endoscopic image may also be provided on display screen (56).

The images provided through display screen (56) may help guide the operator in maneuvering and otherwise manipulating instruments within the patient's head (H). It should also be understood that other components of a surgical instrument and other kinds of surgical instruments, as described below, may incorporate a navigation sensor like the navigation sensor described above.

II. Example of a Distal Endoscope Cap for ENT Instruments

In some instances, it may be desirable to provide a distal endoscope cap configured for selective attachment to a distal end of an ENT instrument for retrofitting or otherwise modifying the ENT instrument to provide the ENT instrument with visualization and/or navigation capabilities. For example, retrofitting the ENT instrument with such a distal endoscope cap may free the shaft of ENT instrument from competing with a separate endoscope shaft for space within small, tortuous anatomical passageways within the patient's head (H). In addition, or alternatively, such a distal endoscope cap may provide visualization of a field of view that is in-line with the operative field at which the ENT instrument is performing treatment, rather than the field of view being offset from the operative field as may be the case when a separate endoscope is used. The example of distal endoscope cap (110) described below may function in such a manner. While the example provided below is discussed in the context of a particular ENT instrument (100), distal endoscope cap (110) may be used to provide navigation capabilities to any other suitable ENT instruments. Other suitable ways in which distal endoscope cap (110) may be used will be apparent to those skilled in the art in view of the teachings herein.

FIGS. 2A-4 show an example of an instrument (100) that may be used to guide a working element (101) (FIG. 2B) into an anatomical passageway, and to which an example of a distal endoscope cap (110) (FIGS. 3-4) may be either removably or permanently attached. As shown in FIG. 2B, working element (101) includes a shaft (102) and an end effector (104). In some versions, working element (101) may include a dilation catheter. In this regard, end effector (104) may have one or more balloons or other dilators, such that instrument (100) may be used to guide end effector (104) of working element (101) into an anatomical passageway to thereby dilate the anatomical passageway. For instance, instrument (100) and working element (101) may be used for dilation of ostia of paranasal sinuses (e.g., to treat sinusitis), dilation of the larynx, dilation of the Eustachian tube, dilation of other passageways within the ear, nose, or throat, etc. In addition, or alternatively, working element (101) may include an RF energy delivery catheter. In this regard, end effector (104) may have one or more RF electrodes, such that instrument (100) may be used to guide end effector (104) of working element (101) into an anatomical passageway to deliver RF energy to tissue in or near the anatomical passageway. For instance, instrument (100) and working element (101) may be used to ablate a nerve (e.g., a posterior nasal neve); ablate a turbinate; or ablate, electroporate (e.g., to promote absorption of therapeutic agents, etc.), or apply resistive heating to any other kind of anatomical structure in the head of a patient. It will be appreciated that working element (101) may include any other suitable type of ENT treatment device.

Instrument (100) of this example includes a handle assembly (106) and a shaft assembly (108). Instrument (100) may be coupled with an inflation fluid source (not shown), which may be operable to selectively supply an inflation fluid to a balloon (not shown) of end effector (104), for inflating the balloon to thereby dilate the anatomical passageway. In addition, or alternatively, instrument (100) may be coupled with an RF generator (not shown), which may be operable to generate RF electrosurgical energy for delivery to tissue via electrodes (not shown) of end effector (104)) to thereby ablate, electroporate, or apply resistive heating to the tissue.

Figure 2A:
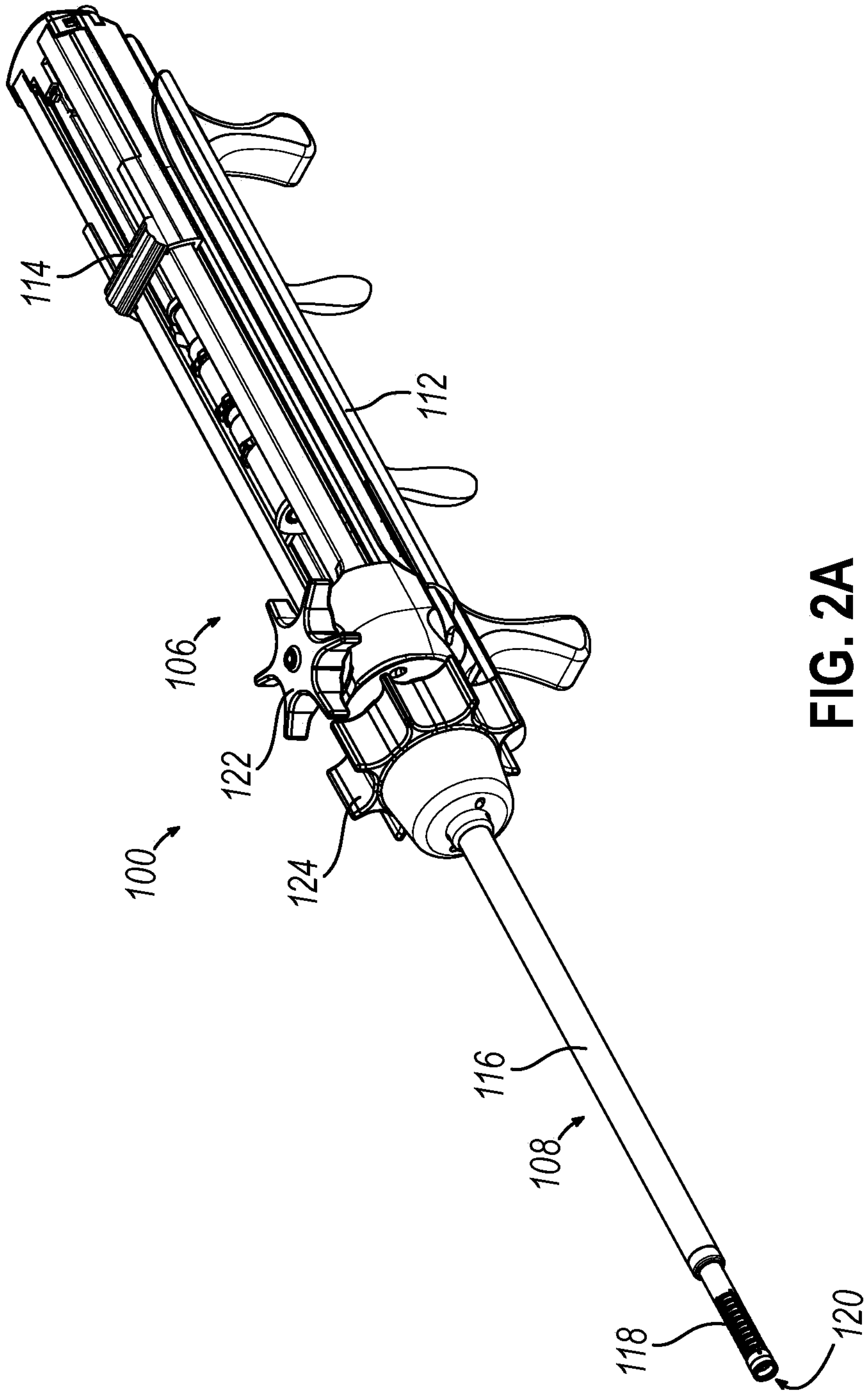
FIG. 2A depicts a front perspective view of an example of an instrument with a slider in a proximal position, such that a working element shaft of the instrument is retracted proximally relative to an open distal end of a shaft assembly of the instrument.
Figure 2B:
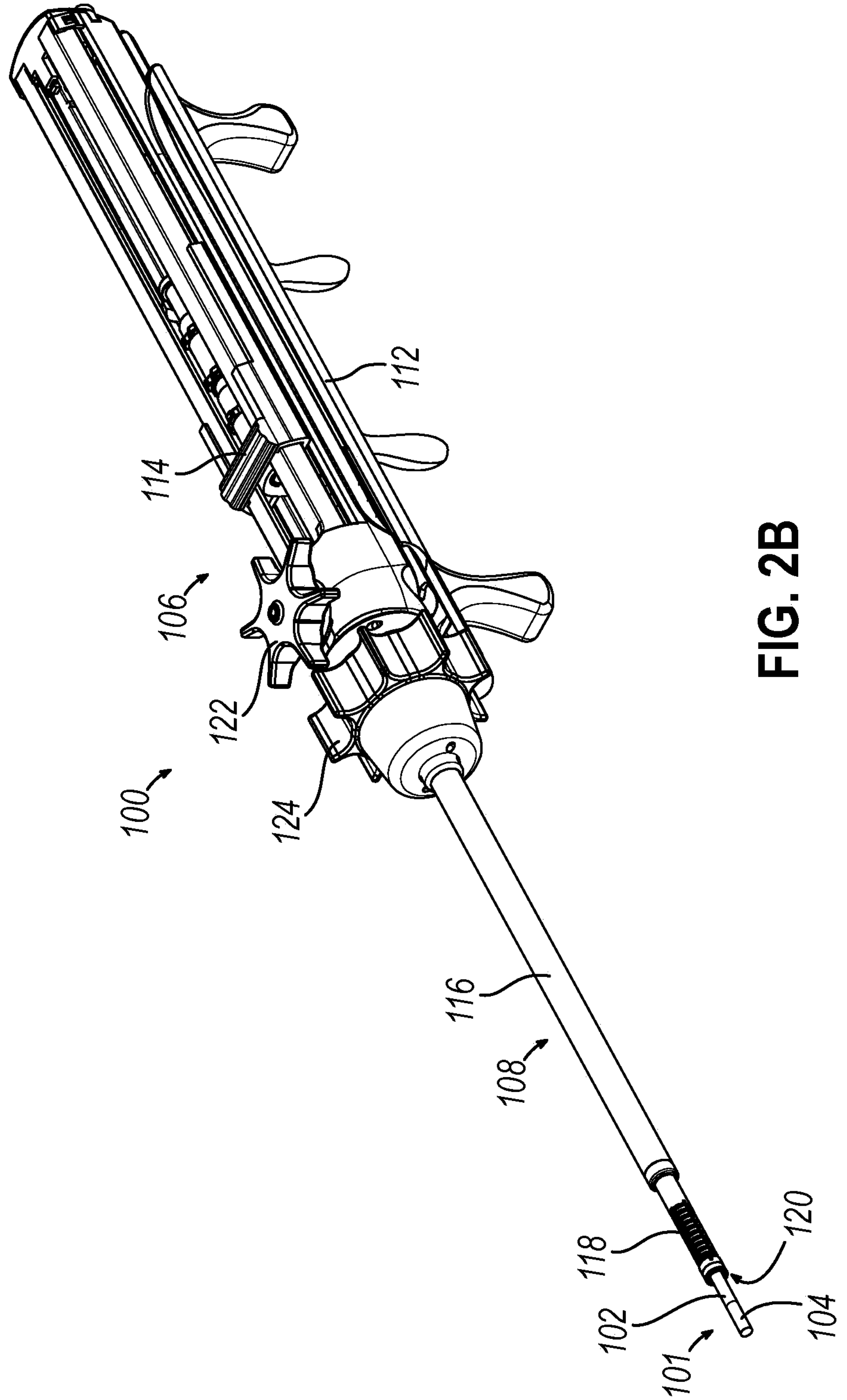
FIG. 2B depicts a front perspective view of the instrument of FIG. 2A, with the slider in a distal position, such that the working element shaft is extended distally relative to the open distal end of the shaft assembly.

Handle assembly (106) of this example includes a body (112) and at least one slider (114). Body (112) is sized and configured to be grasped and operated by a single hand of an operator, such as via a power grip, a pencil grip, or any other suitable kind of grip. Slider (114) is operable to translate longitudinally relative to body (112). Slider (114) is coupled with working element (101) and is thus operable to translate working device (101) longitudinally between a proximally retracted position (FIG. 2A) and a distally extended position (FIG. 2B). In some versions, another slider (not shown) may be operable to translate a guidewire (not shown) longitudinally for directing working device (101) therealong.

Shaft assembly (108) of the present example includes a rigid portion (116), a flexible portion (118) distal to rigid portion (116), and an open distal end (120). A pull-wire (not shown) is coupled with flexible portion (118) and with a deflection control knob (122) of handle assembly (106). Deflection control knob (122) is rotatable relative to body (112), about an axis that is perpendicular to the longitudinal axis of shaft assembly (108), to selectively retract the pull-wire proximally. As the pull-wire is retracted proximally, flexible portion (118) bends and thereby deflects distal end (120) laterally away from the longitudinal axis of rigid portion (116). Deflection control knob (122), the pull-wire, and flexible portion (118) thus cooperate to impart steerability to shaft assembly (108). By way of example only, such steerability of shaft assembly (108) may be provided in accordance with at least some of the teachings of U.S. Pat. Pub. No. 2021/0361912, entitled "Shaft Deflection Control Assembly for ENT Guide Instrument," published Nov. 25, 2021, the disclosure of which is incorporated by reference herein, in its entirety. Other versions may provide some other kind of user input feature to drive steering of flexible portion (118), instead of deflection control knob (122). In some alternative versions, deflection control knob (122) is omitted, and flexible portion (118) is malleable. In still other versions, the entire length of shaft assembly (108) is rigid.

Shaft assembly (108) is also rotatable relative to handle assembly (106), about the longitudinal axis of rigid portion (116). Such rotation may be driven via rotation control knob (124), which is rotatably coupled with body (112) of handle assembly (106). Alternatively, shaft assembly (108) may be rotated via some other form of user input; or may be non-rotatable relative to handle assembly (106). It should also be understood that the example of handle assembly (106) described herein is merely an illustrative example. Shaft assembly (108) may instead be coupled with any other suitable kind of handle assembly or other supporting body.

Figure 3:
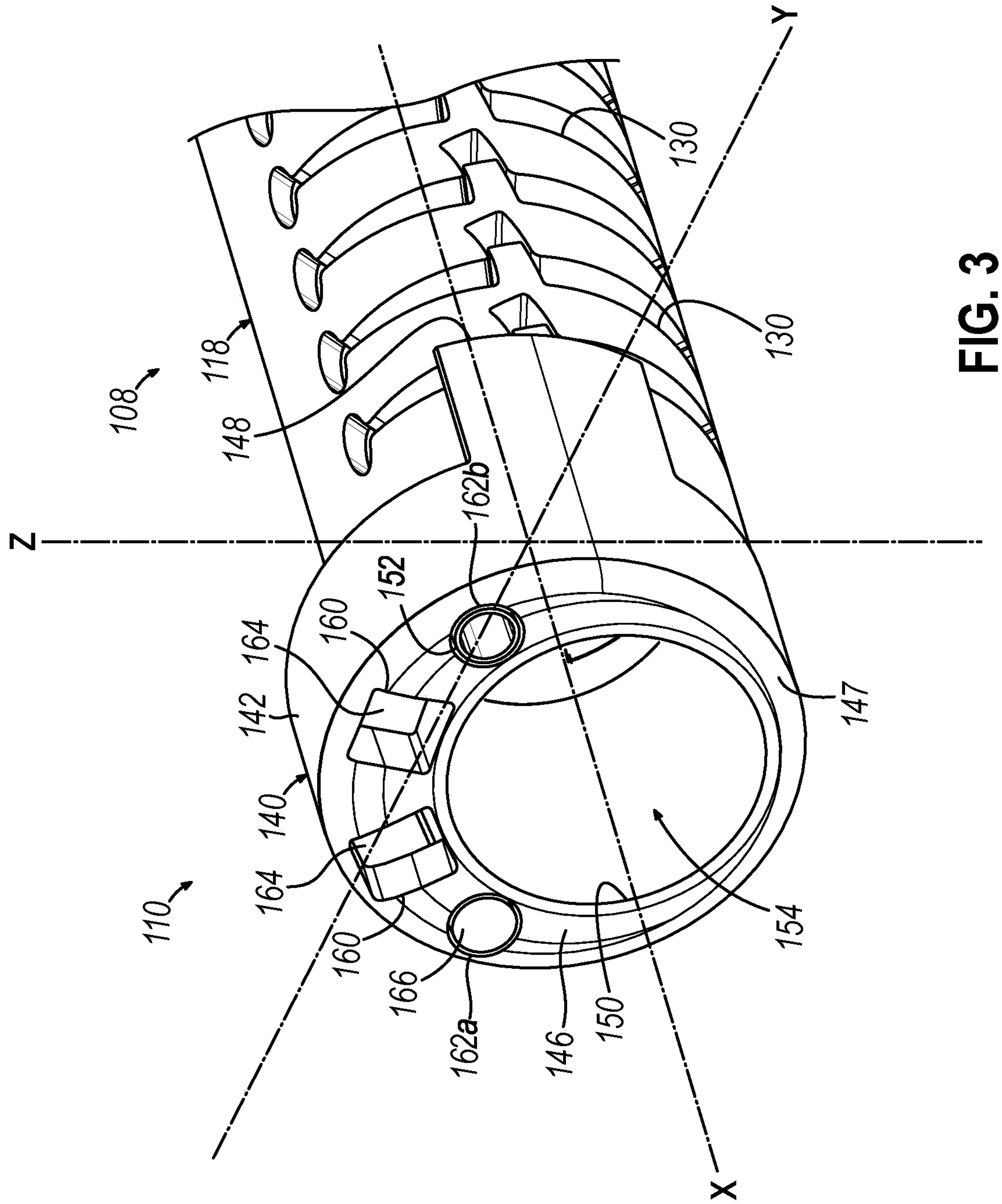
FIG. 3 depicts a front perspective view of a distal portion of the instrument of FIG. 2A, with an example of a distal endoscope cap removably attached to the open distal end of the shaft assembly.
Figure 4:
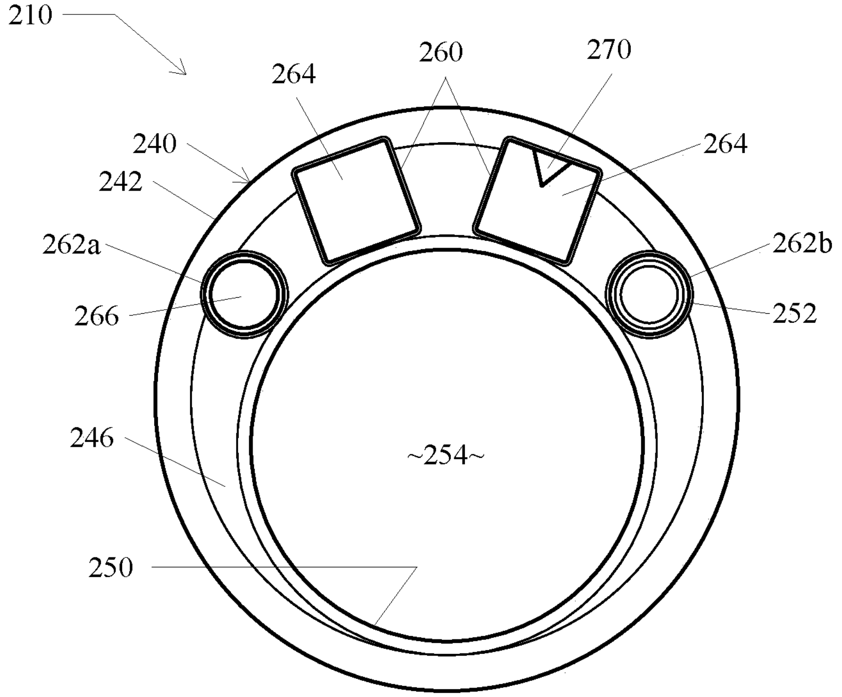
FIG. 4 depicts a front elevation view of another example of a distal endoscope cap for use with the instrument of FIG. 2A and having two cameras, a single illuminating element, and a single navigation sensor, and further having a reference marker positioned within the collective field of view of the cameras.

As best shown in FIGS. 3-4, flexible portion (also referred to as a flexible guide shaft or a deflectable guide shaft) (118) of shaft assembly (108) includes a linear array of articulating ribs (130) connected to each other by a resilient spine (132) for accommodating articulation of articulating ribs (130) relative to rigid portion (116) via the pull-wire described above. To that end, flexible portion (118) also includes a pair of pull-wire coupling holes (134) near open distal end (120) and generally angularly aligned with resilient spine (132) about the longitudinal axis of flexible portion (118) for coupling with a distal end of the pull-wire. A working lumen (not shown) extends longitudinally from an open proximal end (not shown) of shaft assembly (108) all the way to open distal end (120) and is configured to slidably receive working element (101), such that shaft assembly (108) may receive working element (101) at the open proximal end, and such that shaft assembly (108) may guide working element (101) out through open distal end (120). In some versions, the working lumen may have a diameter of about 2.9 mm. Flexible portion (118) of shaft assembly (108) may be formed of a metallic material, such as stainless steel and/or nitinol. In addition, or alternatively, flexible portion (118) may be configured and operable in accordance with any one or more of the teachings of U.S. Pat. No. 11,376,401, entitled "Deflectable Guide for Medical Instrument," issued Jul. 5, 2022, the disclosure of which is incorporated by reference herein.

With continuing reference to FIGS. 3-4, distal endoscope cap (110) is attachable to open distal end (120) of shaft assembly (108) and is operable to provide visualization, navigation, and irrigation capabilities to shaft assembly (108) while allowing shaft assembly (108) to continue to be used to guide working element (101) through open distal end (120).

In this regard, distal endoscope cap (110) of the present example includes a body (140) having a generally cylindrical hub (142) extending between proximal and distal surfaces (144, 146). Distal endoscope cap (110) of the present example includes a fillet (147) between distal surface (146) and a generally cylindrical outer surface of hub (142) to inhibit trauma to tissue encountered by distal endoscope cap (110), such that distal endoscope cap (110) may be considered atraumatic. In the example shown, body (140) also has a pair of laterally-opposed coupling wings (148) extending proximally from proximal surface (144) of hub (142). Body (140) may be constructed of any suitable translucent or opaque material, such as a polymeric material (e.g., plastic) or a metallic material. In the example shown, hub (142) and wings (148) are integrally formed together with each other as a unitary (e.g., monolithic) piece to define body (140). In this regard, body (140) may be manufactured via 3D printing, injection molding, investment casting, machining, and/or any other suitable manufacturing techniques. In some versions, distal endoscope cap (110) may have a maximum outer cross-dimension, such as a maximum outer diameter (e.g., defined by the cylindrical outer surface of hub (142)), less than about 4.3 mm, such as less than about 4.2 mm. In this manner, the maximum outer cross-dimension of distal endoscope cap (110) may be only slightly greater than that of flexible portion (118) of shaft assembly (108) (which may itself be between about 3.6 mm and about 3.7 mm) to avoid interfering with the ability of flexible portion (118) to fit within anatomical passageways when distal endoscope cap (110) is attached thereto.

As shown, each wing (148) of distal endoscope cap (110) includes a laterally inwardly-facing gripping surface (149) configured to frictionally engage a generally cylindrical outer surface of flexible portion (118) of shaft assembly (108) near open distal end (120) for removably attaching distal endoscope cap (110) to open distal end (120). In the example shown, gripping surfaces (149) are spaced apart from each other by a distance substantially equal to or slightly less than a diameter of the cylindrical outer surface of flexible portion (118), and each gripping surface (149) is curved to complement the cylindrical outer surface of flexible portion (118) for enhancing the frictional engagement between each gripping surface (149) and the cylindrical outer surface of flexible portion (118). In some versions, each wing (148) may be configured to flex slightly laterally outwardly during insertion of flexible portion (118) between gripping surfaces (149). While gripping surfaces (149) of wings (148) are shown frictionally engaging the cylindrical outer surface of flexible portion (118), it will be appreciated that distal endoscope cap (110) may be either removably or permanently attached to open distal end (120) in any suitable manner, such as via adhesive, thermal bonding, welding, snap fit, or any other attachment techniques.

Distal endoscope cap (110) of the present example also includes a generally cylindrical bore (150) extending longitudinally between proximal and distal surfaces (144, 146) of hub (142) and configured to be axially aligned with the working lumen of shaft assembly (108) when distal endoscope cap (110) is attached to open distal end (120), such that working element (101) may pass through bore (150) as working element (101) is guided through distal open end (120). Thus, a working channel (154) may extend along bore (150). In some versions, bore (150) may have an inner cross-dimension (e.g., diameter) of between about 2.5 mm and about 2.9 mm. Alternatively, bore (150) may have any other suitable inner cross-dimension.

As used herein, the term "axially aligned" should not be read as necessarily requiring that the central axis of bore (150) must be coaxial with the central axis of the working lumen of shaft assembly (108). Instead, the term "axially aligned" should be read as including arrangements where the central axis of the working lumen of shaft assembly (108) passes through bore (150), with the central axis of the working lumen of shaft assembly (108) being laterally offset from the central axis of bore (150). "Axially aligned" thus includes any arrangements where a working element (101) that is advanced along the working lumen of shaft assembly (108) may ultimately pass through bore (150). Of course, some versions of "axially aligned" arrangements may include arrangements where the central axis of bore (150) is coaxial with the central axis of the working lumen of shaft assembly (108).

Distal endoscope cap (110) of the present example also includes an arch-shaped array of generally rectangular and generally cylindrical bores (160*a*, 160*b*, 162*a*, 162*b*) each extending longitudinally between proximal and distal surfaces (144, 146) of hub (142) and disposed about (e.g., above) bore (150). More particularly, distal endoscope cap (110) includes an inner pair of laterally-opposed, generally rectangular bores (160*a*, 160*b*) and an outer pair of laterally-opposed, generally cylindrical bores (162*a*, 162*b*).

In the example shown, distal endoscope cap (110) further includes a pair of imaging devices (also referred to as image sensors) in the form of cameras (164) received within respective inner bores (160*a*, 160*b*) and a single illuminating element (166) received within first outer bore (162*a*). In some versions, bores (160*a*, 160*b*, 162*a*) may each be sized and shaped to provide a snap fit between the bore (160*a*, 160*b*, 162*a*) and the corresponding camera (164) or illuminating element (166). It will be appreciated that cameras (164) and illuminating element (166) may be fixedly retained within the respective bores (160*a*, 160*b*, 162*a*) in any other suitable manner.

In any event, cameras (164) and illuminating element (166) are configured to cooperate with each other to provide visualization capabilities to shaft assembly (108). Cameras (164) are spaced apart from each other within the respective inner bores (160*a*, 160*b*) to provide stereoscopic visualization of objects within the collective field of view of cameras (164). For example, cameras (164) may capture real-time 3D images of a patient's anatomy and thus enable acquisition of depth-of-field data and/or integration of artificial intelligence programs. In some cases, the images captured by cameras (164) may be superimposed on preoperatively obtained images to provide one or more augmented reality views. In some cases, such an augmented reality view may be updated in real time to reflect anatomical modifications made by working element (101) or other components of instrument (100) (e.g., tissue ablation, dilation, etc.). In addition, or alternatively, cameras (164) may be used to intraoperatively optically track the locations of other components within the patient's anatomy, such as working element (101). Such components may include one or more fiducial markers (not shown) that may be optically recognized via cameras (164). Cameras (164) may thereby provide internal registration of such components. By way of example only, cameras (164) may be configured and operable in accordance with at least some of the teachings of U.S. Pat. No. 10,955,657, entitled "Endoscope with Dual Image Sensors," issued Mar. 23, 2021, the disclosure of which is incorporated by reference herein; U.S. Pat. No. 11,633,083, entitled "3D Scanning of Nasal Tract with Deflectable Endoscope," issued Apr. 25, 2023, the disclosure of which is incorporated by reference herein; and/or U.S. Pat. No. 11,457,981, entitled "Computerized Tomography (CT) Image Correction Using Position and Direction (P&D) Tracking Assisted Optical Visualization," issued Oct. 4, 2022, the disclosure of which is incorporated by reference herein. In some cases, the centers of cameras (164) may be spaced apart from each other by a distance of between about 1 mm and about 2 mm. In the example shown, cameras (164) are oriented relative to each other along a curve defined by the arch-shaped array of generally rectangular bores (160*a*, 160*b*, 162*a*, 162*b*) and may each be at least slightly recessed proximally relative to distal surface (146) of hub (142), as described in greater detail below.

Each camera (164) may have a plurality of leads (not shown) on a proximal end thereof configured to be operatively coupled to processor (52) and/or electrically coupled to a power source (not shown) via respective traces or wires (not shown) extending proximally through the respective bore (160*a*, 160*b*) and along shaft assembly (108) to the coupling unit, for example. Each camera (164) of the present version is fixedly retained within the respective inner bore (160*a*, 160*b*). In some cases, one or more alignment protrusions may be provided in each inner bore (160*a*, 160*b*) for abutting the respective camera (164) to promote positioning of each camera (164) at a predetermined longitudinal position.

Illuminating element (166) is configured and operable to illuminate the field of view of cameras (164). Illuminating element (166) is positioned outboard relative to the adjacent camera (164). While just one illuminating element (166) is used in the present example, other versions may employ two illuminating elements (166) or more than two illuminating elements (166). In some versions, illuminating element (166) may include fiber optic components, such as a lens that is optically coupled with one or more respective optical fibers or optical fiber bundles. Such optical fibers or optical fiber bundles may extend along shaft assembly (108) and be optically coupled with a source of light that is either integrated into handle assembly (106) (or some other body from which shaft assembly (108) extends) or otherwise provided. In addition, or alternatively, illuminating element (166) may include an LED and/or a laser.

While bores (160*a*, 160*b*, 162*a*) are shown for receiving cameras (164) and illuminating element (166), it will be appreciated that cameras (164) and illuminating element (166) may be coupled to body (140) in any other suitable manner. For example, distal endoscope cap (110) may include an arch-shaped array of recesses (not shown) extending radially outwardly from bore (150) and longitudinally between proximal and distal surfaces (144, 146) of hub (142) in place of bores (160*a*, 160*b*, 162*a*). Such recesses may each be configured to receive a corresponding camera (164) or illuminating element (166). In some versions, the recesses may each be sized and shaped to provide a snap fit between the recess and the corresponding camera (164) or illuminating element (166). It will be appreciated that such recesses may enable each camera (164) and illuminating element (166) to be initially inserted together with the respective wires and/or optical fibers (not shown) longitudinally through bore (150), then pressed radially outwardly into the corresponding recess.

As shown, distal endoscope cap (110) of the present example also includes a single navigation sensor (152), which is received within second outer bore (162*b*) and configured to provide navigation capabilities to shaft assembly (108). Navigation sensor assembly (152) includes at least one electromagnetic coil (not shown) operable to generate signals indicative of the position of the respective coil and thereby indicative of distal endoscope cap (110) and/or a portion of shaft assembly (108) (e.g., flexible portion (118)) in three-dimensional space when positioned within an alternating electromagnetic field generated by field generators (64). The position data generated by such position related signals may be processed by processor (52) for providing a visual indication to the operator to show the operator where shaft assembly (108) of instrument (100) is located within the patient (P) in real time. Such a visual indication may be provided as an overlay on one or more preoperatively obtained images (e.g., CT scans) of the patient's anatomy. Navigation sensor assembly (152) may be configured as a single-axis sensor (SAS) (e.g., having a single electromagnetic coil wound about a single axis), as a dual-axis sensor (DAS) (e.g., having two electromagnetic coils wound about respective axes), or as a triple-axis sensor (TAS) (e.g., having three electromagnetic coils wound about respective axes). In addition, or alternatively, navigation sensor assembly (152) may be configured as a flexible printed circuit board (PCB). By way of example only, navigation sensor assembly (152) may be configured and operable in accordance with at least some of the teachings of U.S. Pub. No. 2022/0257093, entitled "Flexible Sensor Assembly for ENT Instrument," published Aug. 18, 2022, the disclosure of which is incorporated by reference herein, in its entirety.

In some cases, a second illuminating element (166) may also be received within second outer bore (162*b*) and may be provided in the form of a lens that is optically coupled with one or more respective optical fibers or optical fiber bundles. In some such cases, navigation sensor (152) may be disposed (e.g., wrapped) about the optical fiber(s) or optical fiber bundle(s) of the second illuminating element (166).

In some other versions, navigation sensor assembly (152) may be suitably sized to fit within bore (150) while still permitting space for working channel (154) to extend along bore (150) (e.g., radially inwardly relative to navigation sensor assembly (152)), thereby permitting additional instrumentation (e.g., working element (101)), suction, fluids, etc. to pass between working channel (154) and the working lumen of shaft assembly (108). In this regard, navigation sensor assembly (152) may be disposed along a generally cylindrical inner surface of bore (150) and may have a generally curved configuration such that navigation sensor assembly (152) is curved about the longitudinal axis of flexible portion (118) of shaft assembly (108) with a radius of curvature corresponding to that of the cylindrical inner surface to thereby conform to an inner circumference of bore (150).

Alternatively, navigation sensor assembly (152) may be disposed along a generally cylindrical outer surface of hub (142) of distal endoscope cap (110), such as along either a top or bottom portion of the cylindrical outer surface of hub (142), and may have a generally curved configuration such that navigation sensor assembly (152) is curved about the longitudinal axis of hub (142) of distal endoscope cap (110) with a radius of curvature corresponding to that of the cylindrical outer surface to thereby conform to an outer circumference of hub (142). In other versions, navigation sensor assembly (152) may be disposed between flexible portion (118) of shaft assembly (108) and distal endoscope cap (110), or within an at least partially annular slot (not shown) extending at least partially through hub (142) of distal endoscope cap (110). In such cases, working channel (154) may be defined by the generally cylindrical inner surface of bore (150). In some versions, body (140) may be configured to electrically isolate the electromagnetic coil(s) of navigation sensor assembly (152) from flexible portion (118) of shaft assembly (108) to inhibit electrical shorting between the electromagnetic coil(s) and flexible portion (118) and/or to inhibit generation of electromagnetic interference or "noise." For example, body (140) may be constructed of an electrically non-conductive (e.g., insulative) material. In some other versions, one or more navigation sensor assemblies (152) may be disposed on one or both wings (148).

In some versions, body (140) may be electrically conductive and configured to deliver RF energy to tissue. For example, body (140) may be coupled with a corresponding one or more wires routed along flexible portion (118) that electrically couple body (140) with an RF generator. Body (140) may thereby serve as an electrode operable to cooperate with a ground pad (not shown) placed in contact with the patient's skin to apply monopolar RF energy to tissue to ablate, electroporate, and/or cauterize the tissue, for example. In some such versions, an electrically insulating material (e.g., plastic, etc.) may be interposed between body (140) and flexible portion (118), such that body (140) may be electrically energized without also energizing flexible portion (118) or other portions of shaft assembly (108).

In some other versions, distal endoscope cap (110) may include one or more electrically conductive elements secured to body (140) and configured to deliver RF energy to tissue. For example, a pair of arcuate conductive elements may be angularly spaced apart from each other on distal surface (146) of hub (142). Such conductive elements may each include any one or more of a conductive wire, plate, film, and/or coating, and may be formed of any suitable material or combination of materials including but not limited to metallic conductive materials such as copper, gold, steel, aluminum, silver, nitinol, etc. and/or non-metallic conductive materials such as conducting polymers, silicides, graphite, etc. Such conductive elements may be secured to body (140) in any suitable fashion, including but not limited to being secured via an adhesive, via vapor deposition, or otherwise, and may be coupled with a corresponding one or more wires routed along flexible portion (118) that electrically couple such conductive elements with an RF generator. The pair of conductive elements may thereby be operable to apply bipolar RF energy to tissue, with one conductive element serving as an active electrode and the other conductive element serving as a return electrode to ablate, electroporate, and/or cauterize the tissue, for example. In some versions, such conductive elements are configured and operable in accordance with at least some of the teachings of U.S. Pub. No. 2022/0110513, entitled "ENT Instrument with Deformable Guide having Translatable Imaging Feature," published Apr. 14, 2022, the disclosure of which is incorporated by reference herein, in its entirety.

While instrument (100) has been described for dilating an anatomical passageway and/or for delivering RF energy to tissue within the ear, nose, or throat of a patient, it will be appreciated that instrument (100) may be adapted to perform other surgical functions including, for example, diagnostic procedures, electrophysiology mapping, electrophysiology directed catheter guided surgery, and/or cardiac ablation procedures, such as via various other types of working elements (101).

III. Examples of Apparatus and Method to Determine Endoscope Roll Orientation Based on Image Analysis As mentioned above, navigation sensor assembly (152) may be configured as a single-axis sensor (SAS). It will be appreciated that in such cases the position related signals generated by the single electromagnetic coil of navigation sensor assembly (152) may be processed by processor (52) to determine the position of distal endoscope cap (110) and/or a distal portion of shaft assembly (108) (e.g., flexible portion (118)) within a coordinate system that is defined by an X-axis (also referred to as a "roll" axis), a Y-axis (also referred to as "pitch" axis), and a Z-axis (also referred to as a "yaw" axis), as shown in FIG. 3. More particularly, the position data generated by such position related signals may be processed by processor (52) to determine the positions of distal endoscope cap (110) and/or the distal portion of shaft assembly (108) along each of the X-axis, Y-axis, and Z-axis. It will also be appreciated that the position related signals generated by the single electromagnetic coil of navigation sensor assembly (152) may be processed by processor (52) to determine one or more orientations of distal endoscope cap (110) and/or the distal portion of shaft assembly (108) within the coordinate system. More particularly, the position data generated by such position related signals may be processed by processor (52) to determine the orientation of distal endoscope cap (110) and/or the distal portion of shaft assembly (108) about the Y-axis, also referred to as the "pitch" of distal endoscope cap (110) and/or the distal portion of shaft assembly (108); and/or to determine the orientation of distal endoscope cap (110) and/or the distal portion of shaft assembly (108) about the Z-axis, also referred to as the "yaw" of distal endoscope cap (110) and/or the distal portion of shaft assembly (108).

In some instances, it may be desirable to provide distal endoscope cap (110) with a feature for determining the orientation of distal endoscope cap (110) and/or the distal portion of shaft assembly (108) about the X-axis, also referred to as the "roll" of distal endoscope cap (110) and/or the distal portion of shaft assembly (108), without necessarily requiring the addition of a second electromagnetic coil, such as via the addition of a second navigation sensor assembly (152) that is also configured as a single-axis sensor (SAS) or via the reconfiguration of navigation sensor assembly (152) as either a dual-axis sensor (DAS) or as a triple-axis sensor (TAS). For example, such a determination of the roll may be utilized by processor (52) to supplement the determinations of the pitch, yaw, and positions along each of the X-axis, Y-axis, and Z-axis provided via the single electromagnetic coil of navigation sensor assembly (152) to thereby provide a comprehensive visual indication of the various positions and orientations of distal endoscope cap (110) and/or the distal portion of shaft assembly (108) within six degrees of freedom.

FIG. 4 shows an example of a distal endoscope cap (210) having such functionality, and which may be incorporated into instrument (100) in place of distal endoscope cap (110). Distal endoscope cap (210) may be similar to distal endoscope cap (110) described above except as otherwise described below. In this regard, distal endoscope cap (210) of the present example includes a body (240) having a generally cylindrical hub (242) extending between a proximal surface (not shown) and a distal surface (246). While not shown, body (240) may have a pair of laterally-opposed coupling wings extending proximally from the proximal surface of hub (242) and similar to wings (148), for example. Body (240) may be constructed of any suitable translucent or opaque material, such as a polymeric material (e.g., plastic) or a metallic material. Hub (242) and the wings may be integrally formed together with each other as a unitary (e.g., monolithic) piece to define body (240). In this regard, body (240) may be manufactured via 3D printing, injection molding, investment casting, machining, and/or any other suitable manufacturing techniques.

Each wing of distal endoscope cap (210) may include a laterally inwardly-facing gripping surface (not shown) configured to frictionally engage a generally cylindrical outer surface of flexible portion (118) of shaft assembly (108) near open distal end (120) for attaching distal endoscope cap (210) to open distal end (120) in a manner similar to that described above. Alternatively, distal endoscope cap (210) may be secured at open distal end (120) using any other suitable structure or techniques.

Distal endoscope cap (210) of the present example also includes a generally cylindrical bore (250) extending longitudinally between the proximal surface and distal surface (246) of hub (242) and configured to be axially aligned with the working lumen of shaft assembly (108) when distal endoscope cap (210) is attached to open distal end (120), such that working element (101) may pass through bore (250) as working element (101) is guided through distal open end (120). Thus, a working channel (254) may extend along bore (250).

Distal endoscope cap (210) of the present example also includes an arch-shaped array of generally rectangular and generally cylindrical bores (260, 262*a*, 262*b*) each extending longitudinally between the proximal surface and distal surface (246) of hub (242) and disposed about (e.g., above) bore (250). More particularly, distal endoscope cap (210) includes an inner pair of laterally-opposed, generally rectangular bores (260) and an outer pair of laterally-opposed, generally cylindrical bores (262*a*, 262*b*). Distal endoscope cap (210) further includes a pair of cameras (264) similar to cameras (164), which are each received within a respective inner bore (260) in a manner similar to that described above; and a single illuminating element (266) similar to illuminating elements (166), which is received within first outer bore (262*a*) in a manner similar to that described above.

While distal endoscope cap (210) includes two cameras (264) in this example, other variations may include only one camera (264). Thus, it is not necessary to include two cameras (264) in all versions. In some versions, illuminating element (266) may include fiber optic components, such as a lens that is optically coupled with one or more respective optical fibers or optical fiber bundles. For example, illuminating element (266) may include an optical fiber having a cross dimension (e.g., diameter) of about 0.020 inch.

As shown, distal endoscope cap (210) of the present example also includes a single navigation sensor (252), which is received within second outer bore (262*b*). More particularly, distal endoscope cap (210) of the present example does not include more than one navigation sensor (252), though it will be appreciated that distal endoscope cap (210) may include more than one navigation sensor (252) in some other versions. In the example shown, navigation sensor (252) is configured as a single-axis sensor (SAS), though it will be appreciated that navigation sensor (252) may alternatively be configured as a dual-axis sensor (DAS), or as a triple-axis sensor (TAS). In addition, or alternatively, navigation sensor (252) may be similar to navigation sensor assembly (152). In some cases, a second illuminating element (266) may also be received within second outer bore (262*b*) and may be provided in the form of a lens that is optically coupled with one or more respective optical fibers or optical fiber bundles. In some such cases, navigation sensor (252) may be disposed (e.g., wrapped) about the optical fiber(s) or optical fiber bundle(s) of the second illuminating element (266).

While the present example includes cameras (264) and navigation sensor (252) in a distal endoscope cap (210), it should be understood that these features (including variations where just one camera (264) is provided) may be provided in other kinds of structures. For instance, some versions of instrument (100) may integrate one or more cameras (264) and a navigation sensor (252) at distal end (120) of shaft assembly (108) in some other kind of structure. It should therefore be understood that a cap (210) is not necessarily required in all versions.

In the example shown, a reference marker in the form of a generally triangular protrusion (270) extends generally downwardly from an upper edge of second inner bore (260*b*) and is distal relative to the corresponding camera (264), such that at least a portion of protrusion (270) extends slightly over a lens of the corresponding camera (264) and is within the collective field of view of cameras (264). In this regard, protrusion (270) may be optically recognizable by one or both cameras (264). For example protrusion (270) may be opaque and may thereby define a relatively small, generally triangular visual obstruction (O) (FIGS. 5A-5B) in one or more images ($I_1$, $I_2$) captured by cameras (264) at or near a periphery of the collective field of view of cameras (264). It will be appreciated that protrusion (270) may be fixed against movement relative to cameras (264), such that visual obstruction (O) may remain at a fixed location within the collective field of view of cameras (264) and may thereby provide a reference point for assisting with determining an orientation of distal endoscope cap (210) and/or a distal portion of shaft assembly (108) (e.g., flexible portion (118)) in three-dimensional space.

In this regard, protrusion (270) may be utilized to determine the orientation of distal endoscope cap (210) and/or the distal portion of shaft assembly (108) about the X-axis, also referred to as the roll of distal endoscope cap (210) and/or the distal portion of shaft assembly (108). For example, processor (52) may be configured to monitor the location of protrusion (270) relative to one or more anatomical landmarks within the collective field of view of cameras (264) and to calculate a roll angle ($\alpha$) of distal endoscope cap (210) and/or the distal portion of shaft assembly (108) based on changes in the location of protrusion (270) relative to such one or more anatomical landmarks.

Figure 5B:
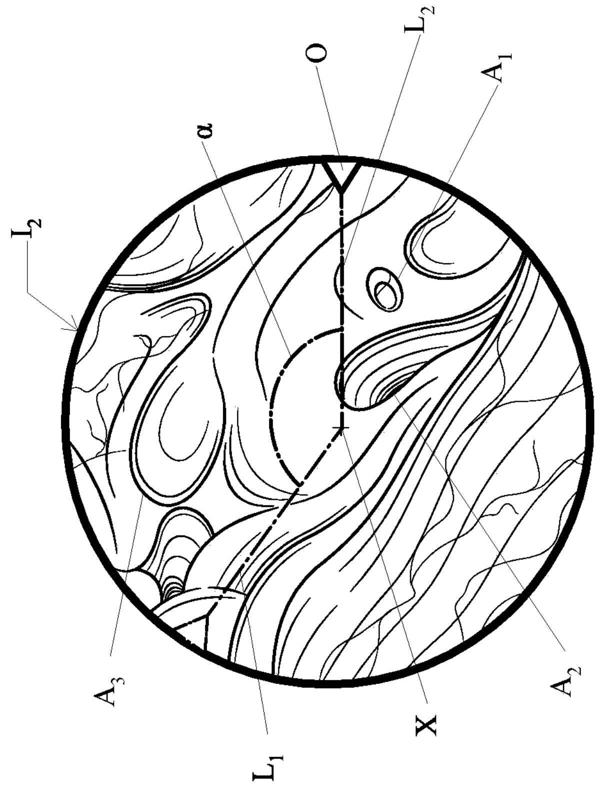
FIG. 5B depicts a schematic view of a second image captured by the cameras of the distal endoscope cap of FIG. 4 while the distal endoscope cap is in a second rotational position about the roll axis.
Figure 5A:
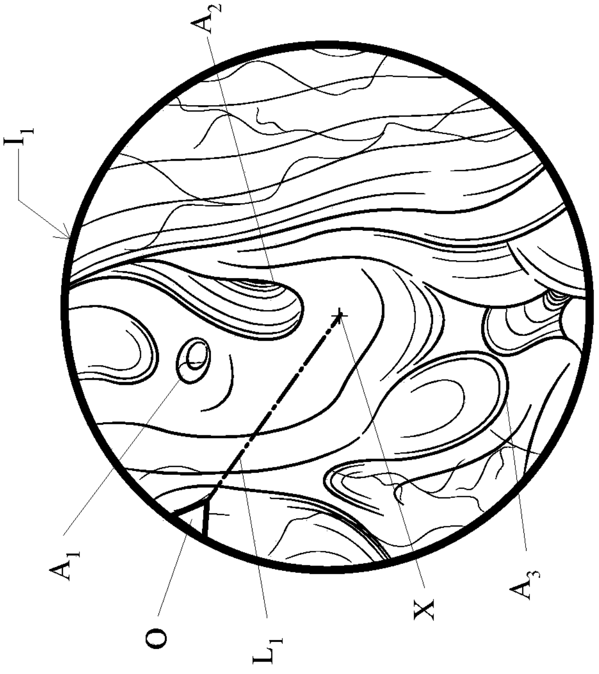
FIG. 5A depicts a schematic view of a first image captured by the cameras of the distal endoscope cap of FIG. 4 while the distal endoscope cap is in a first rotational position about a roll axis.

As shown in FIGS. 5A-5B, cameras (264) may be configured to capture a first image ($I_1$) of a patient's anatomy prior to rolling of distal endoscope cap (210) and/or the distal portion of shaft assembly (108) about the X-axis (FIG. 5A), and to capture a second image ($I_2$) of the patient's anatomy after rolling of distal endoscope cap (210) and/or the distal portion of shaft assembly (108) about the X-axis (FIG. 5B). Processor (52) may be configured to analyze the first and second images ($I_1$, $I_2$), such as using image recognition software, to determine the roll angle ($\alpha$) of distal endoscope cap (210) and/or the distal portion of shaft assembly (108). More particularly, processor (52) may be configured to calibrate the orientation of cameras (264) (and thus of distal endoscope cap (210) and/or the distal portion of shaft assembly (108)) relative to the patient's anatomy based on the location of visual obstruction (O) relative to one or more anatomical landmarks ($A_1$, $A_2$, $A_3$) in the first image ($I_1$). For example, processor (52) may be configured to set the initial roll angle ($\alpha$) to be 0° when the first image ($I_1$) is captured, with visual obstruction (O) at a first location relative to the one or more anatomical landmarks ($A_1$, $A_2$, $A_3$) in the first image ($I_1$).

After the second image ($I_2$) has been captured, processor (52) may be configured to calculate the current roll angle ($\alpha$) by comparing a second location of visual obstruction (O) relative to the one or more anatomical landmarks ($A_1$, $A_2$, $A_3$) in the second image ($I_2$) to the first location of visual obstruction (O) relative to the one or more anatomical landmarks ($A_1$, $A_2$, $A_3$) in the first image ($I_1$). For example, processor (52) may be configured to calculate the current roll angle ($\alpha$) as the angle between a first reference line ($L_1$) extending from the X-axis to the first location of visual obstruction (O) in the first image ($I_1$), and a second reference line ($L_2$) extending from the X-axis to the second location of visual obstruction (O) in the second image ($I_2$). In the example shown in FIG. 5B, the roll angle ($\alpha$) may be about 135°.

In some cases, processor (52) may be configured to provide an overlay of the first and second locations of visual obstruction (O) in the first and second images ($I_1$, $I_2$) via display screen (56). In addition, or alternatively, processor (52) may be configured to display the first line (L1) and/or the first location of visual obstruction (O) in the second image ($I_2$) via display screen (56).

Figure 6:
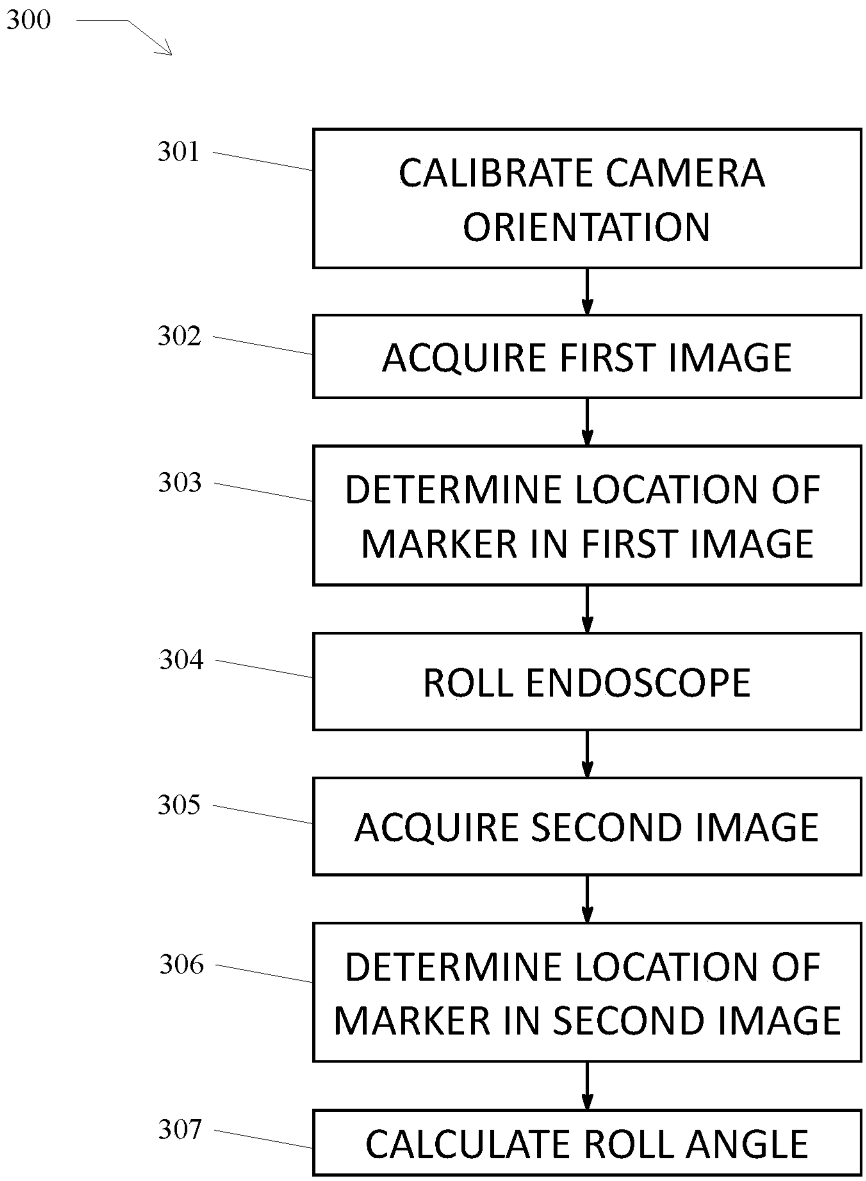
FIG. 6 depicts an example of a method for determining a roll angle of an endoscope using the distal endoscope cap of FIG. 4.

Referring now to FIG. 6, a method (300) for determining the roll angle ($\alpha$) of distal endoscope cap (210) and/or a distal portion of shaft assembly (108) (e.g., flexible portion (118)) is provided. Method (300) includes step (301), at which the orientation of one or more cameras (264) of distal endoscope cap (210) is calibrated. Method (300) proceeds from step (301) to step (302), at which a first image ($I_1$) is acquired via cameras (264), the first image ($I_1$) including any one or more anatomical landmarks ($A_1$, $A_2$, $A_3$) and the visual obstruction (O) defined by protrusion (270). Method (300) proceeds from step (302) to step (303), at which the first location of the visual obstruction (O) defined by protrusion (270) relative to the one or more anatomical landmarks ($A_1$, $A_2$, $A_3$) in the first image ($I_1$) is determined, such as by processor (52) using image recognition software. In some instances, step (303) may be performed prior to step (301), such that step (301) may be performed based on the results of step (303). For example, the orientation of one or more cameras (264) (and thus of distal endoscope cap (210) and/or the distal portion of shaft assembly (108)) may be calibrated relative to the patient's anatomy based on the first location of visual obstruction (O) relative to the one or more anatomical landmarks ($A_1$, $A_2$, $A_3$) in the first image ($I_1$), such as by setting an initial roll angle ($\alpha$) to be 0° when the first image ($I_1$) is captured. A first reference line ($L_1$) may extend from the X-axis to the first location of visual obstruction (O) in the first image ($I_1$).

Method (300) proceeds from step (303) to step (304), at which distal endoscope cap (210) and/or the distal portion of shaft assembly (108) is/are rolled about the X-axis. Method (300) proceeds from step (304) to step (305), at which a second image (I) is acquired via cameras (264), the second image (I) including the any one or more anatomical landmarks ($A_1$, $A_2$, $A_3$) and the visual obstruction (O) defined by protrusion (270). Method (300) proceeds from step (305) to step (306), at which at which the second location of the visual obstruction (O) defined by protrusion (270) relative to the one or more anatomical landmarks ($A_1$, $A_2$, $A_3$) in the second image ($I_2$) is determined, such as by processor (52) using image recognition software. A second reference line ($L_2$) may extend from the X-axis to the second location of visual obstruction (O) in the second image ($I_2$).

Method (300) proceeds from step (306) to step (307), at which the current roll angle ($\alpha$) is calculated, such as by processor (52) calculating the angle between the first and second reference lines ($L_1$, $L_2$). It will be appreciated that method (300) may return from step (307) to step (304) through step (307), such as in cases where further rolling of distal endoscope cap (210) and/or the distal portion of shaft assembly (108) about the X-axis is desired. In this regard, the location of the visual obstruction (O) defined by protrusion (270) relative to the one or more anatomical landmarks ($A_1$, $A_2$, $A_3$) may be continuously monitored as additional images are acquired for continuously calculating the current roll angle ($\alpha$). For example, the current roll angle ($\alpha$) may be calculated by processor (52) calculating the angle between the first reference line ($L_1$) and a current reference line that extends from the X-axis to the current location of visual obstruction (O) in the current image.

In some instances, method (300) may include determining the pitch, yaw, and positions along each of the X-axis, Y-axis, and Z-axis of distal endoscope cap (210) and/or the distal portion of shaft assembly (108), such as via a single electromagnetic coil of navigation sensor assembly (152), and supplementing such determinations with the calculated roll angle ($\alpha$) to thereby provide a comprehensive visual indication of the various positions and orientations of distal endoscope cap (210) and/or the distal portion of shaft assembly (108) within six degrees of freedom.

While the example provided above is discussed in the context of a particular ENT instrument (100) with distal endoscope cap (210), the method may be used in connection with any other suitable ENT instruments and/or endoscopes. Other suitable ways in which the method may be used will be apparent to those skilled in the art in view of the teachings herein.

IV. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising a shaft assembly, the shaft assembly comprising: (a) a working channel sized to receive a working element; (b) a distal end including an opening, the opening being positioned to allow a working element in the working channel to pass through the distal end; (c) an image sensor, the image sensor having a field of view distal to the distal end such that the image sensor is configured to capture at least one image providing a field of view distal to the distal end; (d) a navigation sensor, the navigation sensor being configured to generate signals indicative of a position of the distal end in three-dimensional space; and (e) a reference marker, the reference marker being positioned within the field of view of the image sensor, the reference marker being fixed against movement relative to the image sensor.

EXAMPLE 2

The apparatus of Example 1, the navigation sensor consisting of only a single navigation sensor.

EXAMPLE 3

The apparatus of any of Examples 1 through 2, the navigation sensor comprising a single-axis sensor (SAS).

EXAMPLE 4

The apparatus of any of Examples 1 through 3, the reference marker being positioned distally of the image sensor.

EXAMPLE 5

The apparatus of any of Examples 1 through 4, the reference marker comprising a protrusion.

EXAMPLE 6

The apparatus of any of Examples 1 through 5, the reference marker being optically recognizable by the image sensor.

EXAMPLE 7

The apparatus of Example 6, the reference marker being opaque.

EXAMPLE 8

The apparatus of any of Examples 1 through 7, the reference marker being configured to define a visual obstruction in the at least one image.

EXAMPLE 9

The apparatus of Example 8, the at least one image including a first image in which the visual obstruction is at a first location relative to a structure that is distal to the distal end.

EXAMPLE 10

The apparatus of Example 9, the at least one image including a second image in which the visual obstruction is at a second location relative to the structure that is distal to the distal end, the second location being angularly displaced from the first location relative to a longitudinal axis of the shaft.

EXAMPLE 11

A system, comprising: (a) the apparatus of any of Examples 1 through 10; and (b) a processor, the processor being in operative communication with the image sensor for receiving the at least one image from the image sensor, the processor being in operative communication with the navigation sensor for receiving the signals from the navigation sensor.

EXAMPLE 12

The system of Example 11, the processor being configured to determine a position and orientation of the distal end in three-dimensional space based on the at least one image received from the image sensor and the signals received from the navigation sensor.

EXAMPLE 13

The system of any of Examples 11 through 12, the processor being configured to determine the position of the distal end in three-dimensional space based on the signals received from the navigation sensor.

EXAMPLE 14

The system of any of Examples 11 through 13, the processor being configured to determine each of a pitch angle and a yaw angle of the distal end in three-dimensional space based on the signals received from the navigation sensor.

EXAMPLE 15

The system of any of Examples 11 through 14, the processor being configured to determine a roll angle of the distal end in three-dimensional space based on the at least one image received from the image sensor.

EXAMPLE 16

The system of Example 15, the shaft assembly defining a longitudinal axis, the apparatus further including a body having an actuator, the shaft assembly extending distally from the body, the actuator being operable to rotate the shaft assembly about the longitudinal axis to thereby change the roll angle of the distal end.

EXAMPLE 17

The apparatus of any of Examples 1 through 16, further comprising a distal cap at the distal end.

EXAMPLE 18

The apparatus of Example 17, the image sensor being incorporated into the distal cap.

EXAMPLE 19

The apparatus of any of Examples 17 through 18, the navigation sensor being incorporated into the distal cap.

EXAMPLE 20

The apparatus of any of Examples 17 through 19, the reference marker being incorporated into the distal cap.

EXAMPLE 21

The apparatus of any of Examples 1 through 20, the shaft further including: (a) a proximal portion defining a longitudinal axis; and (b) a flexible portion, the flexible portion being positioned between the proximal portion and the distal end, the flexible portion being operable to deflect the distal end laterally relative to the longitudinal axis.

EXAMPLE 22

The apparatus of Example 21, further comprising an actuator, the actuator being operable to drive deflection of the distal end laterally relative to the longitudinal axis.

EXAMPLE 23

A system comprising: (a) an apparatus comprising: (i) a shaft, the shaft being sized to fit in an anatomical passageway of a patient, the shaft comprising: (A) a working channel, and (B) a distal end, and (ii) a distal assembly at the distal end of the shaft, the distal assembly comprising: (A) an image sensor, the image sensor being configured to capture at least one image of an anatomical structure, (B) a navigation sensor, the navigation sensor being configured to generate signals indicative of a position, a pitch angle, and a yaw angle of the distal assembly in three-dimensional space, and (C) a protrusion configured and positioned to define a visual obstruction in the at least one image; and (b) a processor, the processor being in operative communication with the image sensor for receiving the at least one image from the image sensor, the processor being in operative communication with the navigation sensor for receiving the signals from the navigation sensor.

EXAMPLE 24

The system of Example 23, the at least one image including a first image in which the visual obstruction is at a first location relative to the anatomical structure, the processor being configured to analyze the first image to determine the first location.

EXAMPLE 25

The system of Example 24, the at least one image including a second image in which the visual obstruction is at a second location relative to the anatomical structure, the second location being angularly displaced from the first location relative to a longitudinal axis of the shaft, the processor being configured to analyze the second image to determine the second location.

EXAMPLE 26

The system of Example 25, the processor being configured to determine a roll angle of the distal assembly in three-dimensional space based on a comparison between the first and second locations of the visual obstruction.

EXAMPLE 27

A method of determining a position and orientation of a distal portion of an instrument in three-dimensional space, the instrument having a shaft configured to be inserted into an anatomical passageway of a patient, the method comprising: (a) determining each of the position, a pitch angle, and a yaw angle of the distal portion in three-dimensional space based on signals received from a navigation sensor of the distal member; (b) acquiring a first image of an anatomical structure of the patient from an image sensor of the distal member; (c) determining a first location of a reference marker of the distal member relative to the anatomical structure in the first image; (d) rolling the distal member about a longitudinal axis of the shaft; (e) acquiring a second image of the anatomical structure of the patient from the image sensor; (f) determining a second location of the reference marker relative to the anatomical structure in the second image; and (g) determining a roll angle of the distal member in three-dimensional space based on a comparison between the first and second locations of the reference marker.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising a shaft assembly, the shaft assembly comprising:

(a) a working channel sized to receive a working element;

(b) a distal end including an opening, the opening being positioned to allow a working element in the working channel to pass through the distal end;

(c) an image sensor, the image sensor having a field of view distal to the distal end such that the image sensor is configured to capture at least one image providing a field of view distal to the distal end, the image sensor being fixed relative to the distal end;

(d) a navigation sensor, the navigation sensor being configured to generate signals indicative of a position of the distal end in three-dimensional space; and (e) a reference marker, the reference marker being positioned within the field of view of the image sensor, the reference marker and the image sensor being fixed against movement relative to one another such that the reference marker remains at a fixed location within the field of view of the image sensor thereby providing a reference point for determining an orientation of the distal end of the shaft assembly.

2. The apparatus of claim 1, the navigation sensor consisting of only a single navigation sensor.

3. The apparatus of claim 1, the navigation sensor comprising a single-axis sensor (SAS).

4. The apparatus of claim 1, the reference marker being positioned distally of the image sensor.

5. The apparatus of claim 1, the reference marker comprising a protrusion.

6. The apparatus of claim 1, the reference marker being optically recognizable by the image sensor.

7. The apparatus of claim 6, the reference marker being opaque.

8. The apparatus of claim 1, the reference marker being configured to define a visual obstruction in the at least one image.

9. The apparatus of claim 8, the at least one image including a first image in which the visual obstruction is at a first location relative to a structure that is distal to the distal end.

10. The apparatus of claim 9, the at least one image including a second image in which the visual obstruction is at a second location relative to the structure that is distal to the distal end, the second location being angularly displaced from the first location relative to a longitudinal axis of the shaft assembly.

11. A system, comprising:

(a) the apparatus of claim 1; and (b a processor, the processor being in operative communication with the image sensor for receiving the at least one image from the image sensor, the processor being in operative communication with the navigation sensor for receiving the signals from the navigation sensor.

12. The system of claim 11, the processor being configured to determine a position and orientation of the distal end in three-dimensional space based on the at least one image received from the image sensor and the signals received from the navigation sensor.

13. The system of claim 11, the processor being configured to determine the position of the distal end in three-dimensional space based on the signals received from the navigation sensor.

14. The system of claim 11, the processor being configured to determine each of a pitch angle and a yaw angle of the distal end in three-dimensional space based on the signals received from the navigation sensor.

15. The system of claim 11, the processor being configured to determine a roll angle of the distal end in three-dimensional space based on the at least one image received from the image sensor.

16. The system of claim 15, the shaft assembly defining a longitudinal axis, the apparatus further including a body having an actuator, the shaft assembly extending distally from the body, the actuator being operable to rotate the shaft assembly about the longitudinal axis to thereby change the roll angle of the distal end.

17. The apparatus of claim 1, the shaft assembly further including:

(a) a proximal portion defining a longitudinal axis; and (b) a flexible portion, the flexible portion being positioned between the proximal portion and the distal end, the flexible portion being operable to deflect the distal end laterally relative to the longitudinal axis.

18. The apparatus of claim 17, further comprising an actuator, the actuator being operable to drive deflection of the distal end laterally relative to the longitudinal axis.

19. The apparatus of claim 1, further comprising an illuminating element positioned distal to the image sensor.

20. The apparatus of claim 1, wherein the distal end of the shaft assembly includes a bore that receives the image sensor therein, the bore located outward of the working channel, and the reference marker positioned in the bore distal to the image sensor.

* * * * *